United States Patent [19]

Otani

[11] 4,198,959
[45] Apr. 22, 1980

[54] SEALING DEVICE FOR AN ENDOSCOPE GUIDE WIRE ASSEMBLY

[75] Inventor: Yutaka Otani, Hachioji, Japan

[73] Assignee: Olympus Optical Co., Ltd., Tokyo, Japan

[21] Appl. No.: 918,504

[22] Filed: Jun. 23, 1978

[30] Foreign Application Priority Data

Jun. 30, 1977 [JP] Japan .............................. 52-85410[U]

[51] Int. Cl.² .............................................. A61B 1/00
[52] U.S. Cl. ...................................................... 128/5
[58] Field of Search ........................... 128/3–8, 128/348, 349 B, 349 BV, 303.1, 303.11, 303.15, 305; 403/50, 51, 134, 288; 74/18.2, 502, 18

[56] References Cited

U.S. PATENT DOCUMENTS

| 3,242,868 | 3/1966 | Gold | 74/18.2 |
| 3,368,835 | 2/1968 | Hackforth | 403/50 |
| 3,896,793 | 7/1975 | Mitsui et al. | 128/6 |
| 3,899,829 | 8/1975 | Storm et al. | 128/305 |

FOREIGN PATENT DOCUMENTS

693608 9/1964 Canada ........................... 74/18

2805298 8/1978 Fed. Rep. of Germany .

*Primary Examiner*—Robert W. Michell
*Assistant Examiner*—Jeffrey W. Tayon

[57] ABSTRACT

A sealing device for an endoscope intended to effect sealing between an endoscope guide hole and an operating wire inserted thereinto is set in a medical instrument-leading chamber provided in a distal end portion of an endoscope, and is formed of a substantially hollow cylindrical or trumpet-shaped elastic member. One end of the sealing device is hermetically connected to a wall of the medical instrument-leading chamber to which the endoscope guide hole in the distal end portion is opened. The other end of the sealing device is also hermetically connected to the intermediate point of that portion of the operating wire which projects into the medical instrument-leading chamber from the endoscope guide hole, the operating wire being used to turn a rotary member in order to define the direction in which the forward portion of the medical instrument is to be directed in a body cavity. This arrangement effectively prevents a coelom liquid, washing water or liquid filth from being carried into the endoscope guide hole.

4 Claims, 7 Drawing Figures

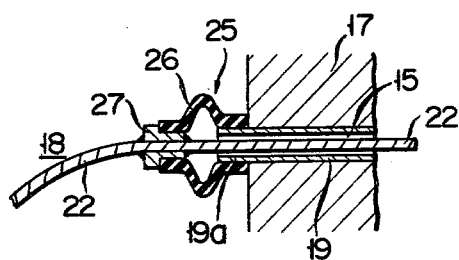
FIG. 4
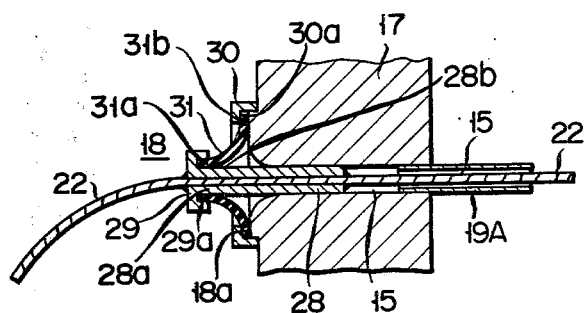
FIG. 5
FIG. 6
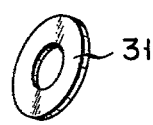
FIG. 7
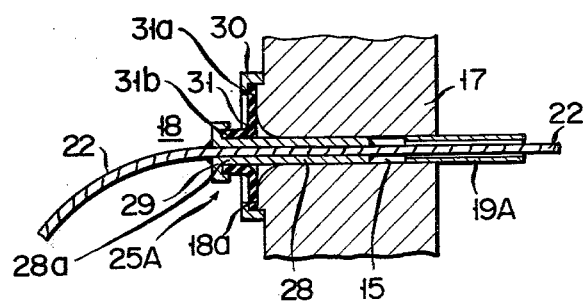

000# SEALING DEVICE FOR AN ENDOSCOPE GUIDE WIRE ASSEMBLY

BACKGROUND OF THE INVENTION

This invention relates to a sealing device for an endoscope, and more particularly to a device for effecting sealing between an endoscope guide hole and an operating wire inserted thereinto, in which the operating wire turns a rotary member disposed in a distal end portion of an endoscope in order to define the direction in which that forward portion of a medical instrument is to be directed in a body cavity.

An endoscope enabling a treating implement (hereinafter referred to as a "medical instrument") such as forceps to be inserted into a body cavity from the distal end generally comprises, as illustrated in FIGS. 1 and 2, an observation optical system 2 and illumination optical system 3 both set in the distal end portion 1, and a leading chamber 5 for a medical instrument 4 provided in the proximity thereof. A rotary member 6 for defining the direction in which the medical instrument 4 is guided into a body cavity is pivoted by a pin 7 to the inner wall of the medical instrument-leading chamber 5. An operating wire 8 is connected to one end of the rotary member 6. When pulled at an operating section positioned in the proximal end portion of an endoscope, the operating wire 8 properly turns the rotary member 6. The operating wire 8 extends to the operating section through a guide hole defined by a different guide pipe 10 from the channel through which the medical instrument 4 is conducted.

With the prior art endoscope, however, the forward end of the guide pipe 10 is opened, as shown in FIG. 2, to the internal space 11 of the medical instrument-leading chamber 5. Further, the operating wire 8 is loosely inserted into the guide pipe 10 for smooth movement therethrough. Consequently, a gap 12 generally arises between the operating wire 8 and the guide pipe 10.

Therefore, the prior art endoscope had the drawbacks that coelom liquid washing water or liquid filth tended to be carried through the gap 12 into the guide pipe 10 during the operation of the endoscope; the gap 12 was too narrow to fully wash off the above-mentioned foreign matter brought into the guide pipe 10 with the resultant failure to carry out full disinfection; and washing water sometimes passed through the gap 12 into the operating section of the endoscope, leading to the damage of the operating section.

SUMMARY OF THE INVENTION

The object of this invention is to provide a sealing device for effecting sealing between a guide hole and an operating wire inserted therethrough within a medical instrument-leading chamber provided in a distal end portion of an endoscope, thereby preventing coelom liquid, liquid filth or washing water from being carried into the guide hole.

The sealing device according to this invention comprises an elastic, generally hollow cylindrical member. One end of the sealing device is hermetically connected to that wall of the medical instrument-leading chamber provided in the distal end portion of an endoscope to which a medical instrument guide hole is opened. The other end of the sealing device is also hermetically connected to the intermediate point of that portion of an operating wire which projects into the medical instrument-leading chamber through an operating wire guide hole. The sealing device of this invention which is made of elastic material very effectively prevents foreign matter such as coelom liquid, washing water and liquid filth from being carried into the operating wire guide hole, without obstructing the smooth movement of the operating wire through its guide hole.

BRIEF DESCRIPTION OF THE DRAWING

FIG. 4 is a longitudinal sectional view showing the operation of the sealing device of the invention when the operating wire of FIG. 3 is pulled toward an operating section of an endoscope;

FIG. 5 is a longitudinal sectional view of a main part of the distal end portion of an endoscope according to another embodiment of this invention;

FIG. 6 is a perspective view of a ring-like member which forms the cylindrical portion of the sealing device of FIG. 5 when it is set in position;

FIG. 7 is a longitudinal sectional view of the sealing device of the invention when the operating wire of FIG. 5 is pulled toward an operating section of an endoscope.

DESCRIPTION OF THE PREFERRED EMBODIMENTS

Figure 3:
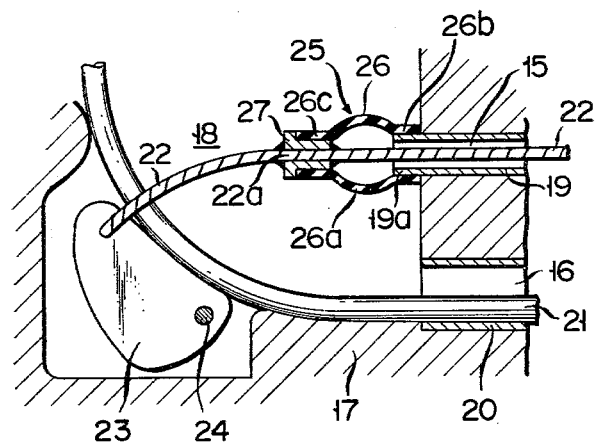
FIG. 3 is a longitudinal sectional view of a main part of the distal end portion of an endoscope provided with a sealing device according to one embodiment of this invention.

Referring to FIGS. 3 and 4, an endoscope is lengthwise penetrated by an operating wire guide hole 15 and a medical instrument channel 16, both of which extend to a medical instrument-leading chamber 18 provided in the distal end portion 17 of the endoscope. Inserted into the operating wire guide hole 15 is a pipe 19, one end 19a of which projects into the medical instrument-leading chamber 18. The medical instrument channel 16 with a pipe 20 inserted thereinto is opened at the forward end to the medical instrument-leading chamber 18. Inserted into the medical instrument channel 16 is an elongate, flexible medical instrument 21 such as forceps, the forward end of which projects through the medical instrument-leading chamber 18 into a body cavity from the lateral side of the distal end portion 17 of the endoscope.

Figure 1:
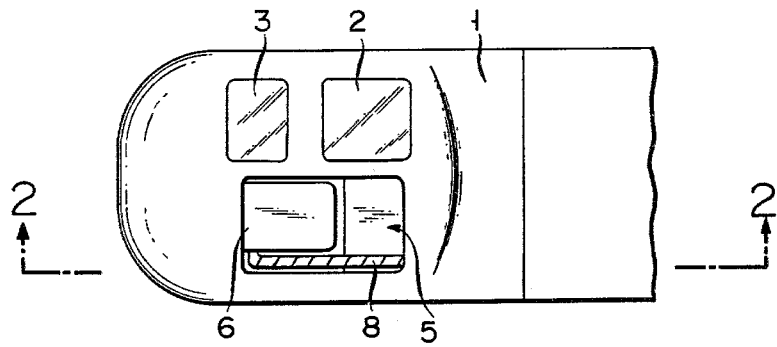
FIG. 1 is a top plan view of a distal end portion of a prior art endoscope.
Figure 2:
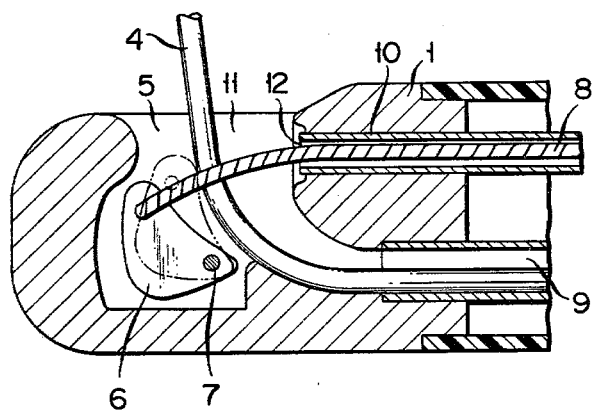
FIG. 2 is a longitudinal sectional view on line 2—2 of FIG. 1.

Inserted into the guide hole 15 is a flexible operating wire 22, the rear end of which extends into an endoscope operating section (not shown), where the operating wire 22 is pushed or pulled. The forward end of the operating wire 22 is drawn into the medical instrument-leading chamber 18 to be fixed to one end of a rotary member 23 constructed like the rotary member 6 of FIGS. 1 and 2 used with the prior art endoscope. The rotary member 23 is pivoted by a pin 24 to the inner wall of the medical instrument-leading chamber 18. The push or pull adjusts the angular position of the rotary member 23, thereby enabling the distal end portion of the medical instrument 21 to be drawn into a body cavity in any desired direction.

There will now be described by reference to FIGS. 3 and 4 a sealing device embodying this invention. The sealing device 25 comprises a generally hollow cylindrical member 26, which surrounds an intermediate part of that section of the operating wire 22 which projects into the medical instrument-leading chamber 18 from the forward end 19a of the pipe 19. The cylindrical member 26 is made of rubber or a highly elastic plastic material, and its intermediate portion 26a is swelled as shown in FIG. 3. That forward end portion 19a of the pipe 19 which projects into the medical instrument-leading chamber 18 is hermetically inserted into the rear end 26b of the cylindrical member 26, for example, by close fitting or adhesive. The forward end 26c of the cylindrical member 26 is mounted on a sleeve-shaped connector 27, into which there is inserted the intermediate part 22a of that portion of the operating wire 22 which projects into the medical instrument-leading chamber 18. In this case, the intermediate part 22a of the operating wire 22 is hermetically fixed to the inner wall of the connector 27, for example, by close fitting or adhesive. The connector 27 is hermetically fixed to the inner wall of the cylindrical member 26 by the same process. Accordingly, the cylindrical member 26 and the operating wire 22 are hermetically connected together. Thus, the guide hole 15 is sealed from the medical instrument-leading chamber 18, thereby preventing coelom liquid, liquid filth, or washing water from being carried from the medical instrument-leading chamber 18 into the guide hole 15.

Where the operating wire 22 is pulled in the endoscope operating section (not shown), then the intermediate part 26a of the cylindrical member 26 easily swells out radially due to its elasticity and lengthwise contracts itself, as shown in FIG. 4. Where the operating wire 22 is pushed in the endoscope operating section, then the intermediate part 26a of the cylindrical member 26 has its diameter easily reduced radially and is elongated lengthwise to return to the configuration as shown in FIG. 3. Therefore, the sealing device 25 is not harmfully affected at all by the push and pull of the operating wire 22. Moreover, sealing between the operating wire 22 and guide hole 15 is ensured in spite of the above-mentioned deformation of the cylindrical member 26.

FIGS. 5 to 7 indicate a sealing device according to another embodiment of this invention. The same parts of this embodiment as those of the embodiment of FIGS. 3 and 4 are respectively denoted by the same numerals. The forward end of a pipe 19A is slightly inserted into the guide hole 15 from the rear end of the distal end portion of the endoscope.

A sealing device 25A according to the second embodiment of FIGS. 5 to 7 comprises a sleeve-shaped connector 28 through which the operating wire 22 is drawn fixedly and hermetically and which is slidably inserted from the medical instrument-leading chamber 18 into the guide hole 15. The sealing device 25A comprises a bell-shaped hollow cylindrical member 31 which is positioned between a first flange 29 formed on that end 28a of the connector 28 which faces the medical instrument-leading chamber 18 and a second flange 30 mounted on that wall 18a of the medical instrument-leading chamber 18 which is bored with the guide hole 15 such that the flange 30 surrounds the guide hole 15. The member 31 of the sealing device 25A is made of rubber or highly elastic plastic material, and takes the ring form in a natural condition, as shown in FIG. 6, namely, where it is not subject to any external force. Where required, the member 31 may originally be fabricated into the bell-shape instead of the ring form of FIG. 6. The smaller end 31a and the larger end 31b of the member 31 are hermetically pressed in an annular groove 29a of the flange 29 or bonded by adhesive to the outer surface 28b of the connector 28, and also pressed in an annular groove 30a of the flange 30 or bonded to that portion of the wall 18a of the medical instrument-leading chamber 18 which surrounds the guide hole 15. Therefore, sealing is ensured between the operating wire 22 and flange 29, as well as between the member 31 and guide hole 15, thereby preventing coelom liquid, liquid filth or washing water from being carried from the medical instrument-leading member 18 into the guide hole 15.

Where the operating wire 22 is pulled in the endoscope operating section (not shown), then the connector 28 is drawn into the guide hole 15 while sliding along the inner wall thereof. At this time, the central portion of the elastic body 31 has its radius of curvature reduced by the pulling force of the operating wire 22, causing both sides of the central portion of member 31 to be easily deformed so as to approach the periphery of the connector 28 and the wall 18a of the medical instrument-leading chamber 18. Therefore, no obstruction takes place in the pulling of the operating wire 22. Where the operating wire 22 is pushed, the member 31 makes a reverse deformation, thus ensuring the smooth movement of the operating wire 22. During the above-mentioned deformation of the member 31, the guide hole 15 is sealed from the medical instrument-leading chamber 18.

What is claimed is:

1. In an endoscope comprising a medical instrument-leading chamber in a distal end portion thereof, a guide hole extending through said distal end portion, an operating wire passing through said guide hole and having one end portion extending through said chamber and a sealing device disposed in said chamber for effecting sealing between said chamber and said guide hole, the improvement wherein said sealing device comprises:
   an elongated hollow cylindrical connector hermetically and reciprocatingly inserted into said guide hole and hermetically and firmly holding said operating wire inserted thereinto, said connector having one end portion projecting in said chamber; and
   an elastic bell-shaped member surrounding said one end portion of said connector and having a smaller end and a larger end, said smaller end being hermetically connected to said one end portion of said connector and said larger end being hermetically connected to said distal end portion.

2. The sealing device according to claim 1, wherein said one end portion of said connector has a lateral outer surface, a first flange is provided on said lateral surface for hermetically holding said smaller end of said bell-shaped member, and a second flange is provided on said distal end portion in said chamber and surrounds said one end portion of said connector for hermetically holding said larger end of said bell-shaped member.

3. The sealing device according to claim 1, wherein said smaller end of said bell-shaped member is bonded to said one end portion of said connector, and said larger end of said bell-shaped member is bonded to said distal end portion in said chamber.

4. The sealing device according to claim 1, wherein said smaller end and said larger end of said bell-shaped member are respectively pressed into said first flange and said second flange.

* * * * *